(12) United States Patent
Shiraishi

(10) Patent No.: US 10,238,365 B2
(45) Date of Patent: Mar. 26, 2019

(54) ULTRASOUND PROBE

(71) Applicant: Hitachi, Ltd., Tokyo (JP)

(72) Inventor: Tomohiro Shiraishi, Tokyo (JP)

(73) Assignee: Hitachi, Ltd., Tokyo (JP)

( * ) Notice: Subject to any disclaimer, the term of this patent is extended or adjusted under 35 U.S.C. 154(b) by 0 days.

(21) Appl. No.: 15/736,958

(22) PCT Filed: Mar. 11, 2016

(86) PCT No.: PCT/JP2016/057825
§ 371 (c)(1),
(2) Date: Dec. 15, 2017

(87) PCT Pub. No.: WO2017/006590
PCT Pub. Date: Jan. 12, 2017

(65) Prior Publication Data
US 2018/0177490 A1    Jun. 28, 2018

(30) Foreign Application Priority Data

Jul. 7, 2015  (JP) ................. 2015-136171

(51) Int. Cl.
*A61B 8/00*   (2006.01)
*A61B 8/06*   (2006.01)
(Continued)

(52) U.S. Cl.
CPC .............. *A61B 8/4483* (2013.01); *A61B 8/06* (2013.01); *A61B 8/4444* (2013.01); *A61B 8/488* (2013.01); *H04R 17/00* (2013.01); *H04R 2440/01* (2013.01)

(58) Field of Classification Search
CPC ...... A61B 8/4483; A61B 8/4444; A61B 8/488
See application file for complete search history.

(56) References Cited

U.S. PATENT DOCUMENTS 5,732,706 A * 3/1998 White .................. A61B 8/4483
600/437
6,044,533 A   4/2000 Bureau et al.
(Continued)

FOREIGN PATENT DOCUMENTS

JP    S63234953 A    9/1988
JP    H060013032 B   2/1994
(Continued)

*Primary Examiner* — J. San Martin

(57) ABSTRACT

Disclosed is an ultrasound probe wherein a backing having built-in lead arrays is disposed on the rear surface side of a transducer array, and backing terminal arrays connected to the lead arrays are provided on the lower surface of the backing. A relay substrate is provided between the backing and an electronic substrate. The relay substrate is provided with electrode section arrays corresponding to the backing terminal arrays. An electrode section includes: a substrate terminal connected to a backing terminal; a via for substrate internal wiring, said via being formed at a position shifted from the substrate terminal; and a conducting path that connects the substrate terminal and the via to each other. The electrode section arrays include a transmission electrode section array, and a reception electrode section array. The shift direction of the transmission electrode section array and that of the reception electrode section array are different from each other.

5 Claims, 12 Drawing Sheets

(51) Int. Cl.
*H04R 17/00* (2006.01)
*A61B 8/08* (2006.01)

(56) References Cited

U.S. PATENT DOCUMENTS

| | | | |
|---|---|---|---|
| 6,522,051 B1 * | 2/2003 | Nguyen | B06B 1/0629 |
| | | | 310/336 |
| 2005/0140248 A1 * | 6/2005 | Kuniyasu | B06B 1/0629 |
| | | | 310/334 |
| 2010/0025785 A1 * | 2/2010 | Robinson | B06B 1/0622 |
| | | | 257/416 |
| 2010/0317972 A1 * | 12/2010 | Baumgartner | G10K 11/002 |
| | | | 600/459 |
| 2013/0214641 A1 * | 8/2013 | Eggen | A61B 8/4483 |
| | | | 310/314 |
| 2015/0276685 A1 | 10/2015 | Yasuhara et al. | |

FOREIGN PATENT DOCUMENTS

| | | |
|---|---|---|
| JP | H09238939 A | 9/1997 |
| JP | H10512680 A | 12/1998 |
| JP | 2002345094 A | 11/2002 |
| JP | 2006020297 A | 1/2006 |
| JP | 3822829 B | 9/2006 |
| JP | 5480988 B1 | 4/2014 |

\* cited by examiner

ULTRASOUND PROBE

CROSS-REFERENCE TO RELATED APPLICATIONS

This application is a national phase claiming the benefit of and priority to International Patent Application No. PCT/JP2016/057825, entitled "ULTRASOUND PROBE", filed Mar. 11, 2016, which claims priority to Japanese Patent Application No. 2015-136171, filed Jul. 7, 2015, which are hereby incorporated by reference in their entireties.

TECHNICAL FIELD

The present disclosure relates to an ultrasound probe, in particular, to an ultrasound probe used to perform a continuous wave Doppler mode.

BACKGROUND

Recently, ultrasound diagnosis apparatuses capable of three-dimensional measurement has started to be widely used. These ultrasound diagnosis apparatuses include an ultrasound probe having, for example, 2D array transducers. Such a probe generally includes a probe head which has 2D array transducers, a probe cable, and a probe connector. An electronic circuit (IC) may be disposed in the probe head. The electronic circuit is, for example, a channel reduction circuit, i.e., a circuit used to reduce the number of signal lines. A relay board as an interposer may be disposed in the probe head. The relay board is a member used to electrically connect two or more transducers of the 2D array transducers and two or more electrode pads provided on an electronic circuit.

Patent Literature 1 discloses an ultrasound probe which includes an electronic circuit in a probe head.

Patent Literature 2 discloses a backing in which two or more leads electrically connected to transducers are embedded. The leads intersect with each other inside the backing.

Patent Literature 3 discloses an ultrasound probe used to perform a continuous wave Doppler mode. This ultrasound probe includes a partition made of a conductive material inserted between a piezoelectric material for transmission and a piezoelectric material for reception to use one of the sides of each piezoelectric material as a common potential.

CITATION LIST

Patent Literature

Patent Literature 1: JP 5480988B
Patent Literature 2: JP 3822829B
Patent Literature 3: Japanese Patent Publication. No. H06-13032

SUMMARY

Technical Problem

In general, in performing a continuous wave Doppler mode, 2D array transducers are divided into a transmitter group and a receiver group. In such a case, because of electrical crosstalk between transmission signals and reception signals, noise may be easily mixed into, in particular, respective reception signals. Each transmission signal has an amplitude level of, for example, about several tens of V, whereas each reception signal has an amplitude level of, for example, about several tens of mV. This difference is significant. Accordingly, electrical crosstalk noise which is caused by transmission signals may be a problem. A reduction of the electrical crosstalk in a relay board, which is a key element on wiring, is particularly desired.

An object of the present disclosure is to reduce electrical crosstalk in an ultrasound probe used to perform a continuous wave Doppler mode

Solution To Problem

An ultrasound probe according to the present disclosure includes two or more transducers; a hacking including a backing body which absorbs ultrasound waves emitted from the two or more transducers, a lead array disposed inside the backing body, the lead array electrically connected to the two or more transducers, and a backing terminal array disposed on a surface of the backing body, the backing terminal array electrically connected to the lead array; an electronic circuit which processes at least one of transmission signals supplied to the two or more transducers and reception signals output from the two or more transducers; and a relay board disposed between the backing and the electronic circuit, the relay board including an electrode array including two or more electrodes. The electrode array includes a first electrode array disposed on one side of a boundary, and a second electrode array disposed on the other side of the boundary. The first electrode array includes a first board terminal sub-array in contact with a first backing terminal sub-array in the backing terminal array, a first via sub-array for substrate internal wiring, the first via sub-array having a two-dimensional arrangement corresponding to a two-dimensional arrangement of the first board terminal sub-array shifted in parallel in a first direction, and a first conductive channel sub-array connecting the first board terminal sub-array and the first via sub-array. The second electrode array includes a second board terminal sub-array in contact with a second backing terminal sub-array in the backing terminal array, a second via sub-array for substrate internal wiring, the second via sub-array having a two-dimensional arrangement corresponding to a two-dimensional arrangement of the second board terminal sub-array shifted in parallel in a second direction, and a second conductive channel sub-array connecting the second board terminal sub-array and the second via sub-array. The first direction is a direction away from the boundary on one side and the second direction is the other direction away from the boundary on the other side.

In the above structure, the electrode array disposed on the relay board includes the first electrode array and the second electrode array. In the first electrode array, the first via sub-array is disposed at a position where the first board terminal sub-array is shifted in parallel in a first direction. In the second electrode array, the second via sub-array is disposed at a position where the second board terminal sub-array is shifted in parallel in a second direction. The first direction is a direction away from the boundary on one side, whereas the second direction is a direction away from the boundary on the other side. In this way, between the first electrode array and the second electrode array, for example, the distance between the vias and the distance between the board terminals and the vias become longer than when the first electrode array and the second electrode array are arranged in an identical layout. Thus, electrical crosstalk between the first electrode array and the second electrode array can be prevented or reduced. Specifically, between the first electrode array and the second electrode array, electrical crosstalk between the vias and between the board terminals and vias can be prevented or reduced. Possible causes of the electrical crosstalk are, for example, a capacitive coupling and inductive coupling between electrodes. In the above structure, because the distance between the vias and the distance between the board terminals and vias can be longer between the first electrode array and the second electrode array, such coupling can be prevented or reduced. Accordingly, electrical crosstalk can be prevented or reduced. The electronic circuit is, for example, a channel reduction circuit. The electronic circuit may be at least one of a transmission signal generator circuit and a reception signal processor circuit. The two or more transducers may be, for example, a 2D transducer array or another type of transducers.

It is preferable that the first direction is oblique to a direction orthogonal to the boundary, and the second direction is oblique to the direction orthogonal to the boundary.

It is preferable that a ground terminal column is disposed at the boundary. This structure can provide a shield effect with the ground terminal column. In this way, electrical crosstalk between the first electrode array and the second electrode array can be further reduced.

It is preferable that an acoustic separation groove is formed at the boundary. In this structure, because the first electrode array and the second electrode array are physically separated, acoustic crosstalk between the first electrode array and the second electrode array can be prevented or reduced. A possible cause of the acoustic crosstalk is that ultrasound waves propagate through a continuous member, and escape into an adjacent element. Because the first electrode array and the second electrode array are physically separated by the acoustic separation groove in the above structure, the propagation of the ultrasound waves is blocked at that portion. In this way, the acoustic crosstalk between the first electrode array and the second electrode array can be prevented or reduced.

It is preferable that the acoustic separation groove is filled with an acoustic separation material. Because the first electrode array and the second electrode array are physically separated in this structure also, the acoustic crosstalk between the first electrode array and the second electrode array can be prevented or reduced.

It is preferable that the lead array includes a first lead sub-array electrically connected to the first backing terminal sub-array, and a second lead sub-array electrically connected to the second backing terminal sub-array. The first lead sub-array and the second lead sub-array are arranged away from each other. In this structure, electrical crosstalk in the lead array can be prevented or reduced between the first lead sub-array and the second lead sub-array.

Advantageous Effects of Invention

According to the present disclosure, electrical crosstalk can be reduced in an ultrasound probe used to perform a continuous wave Doppler mode.

DESCRIPTION OF EMBODIMENTS

First Embodiment

Figure 1:
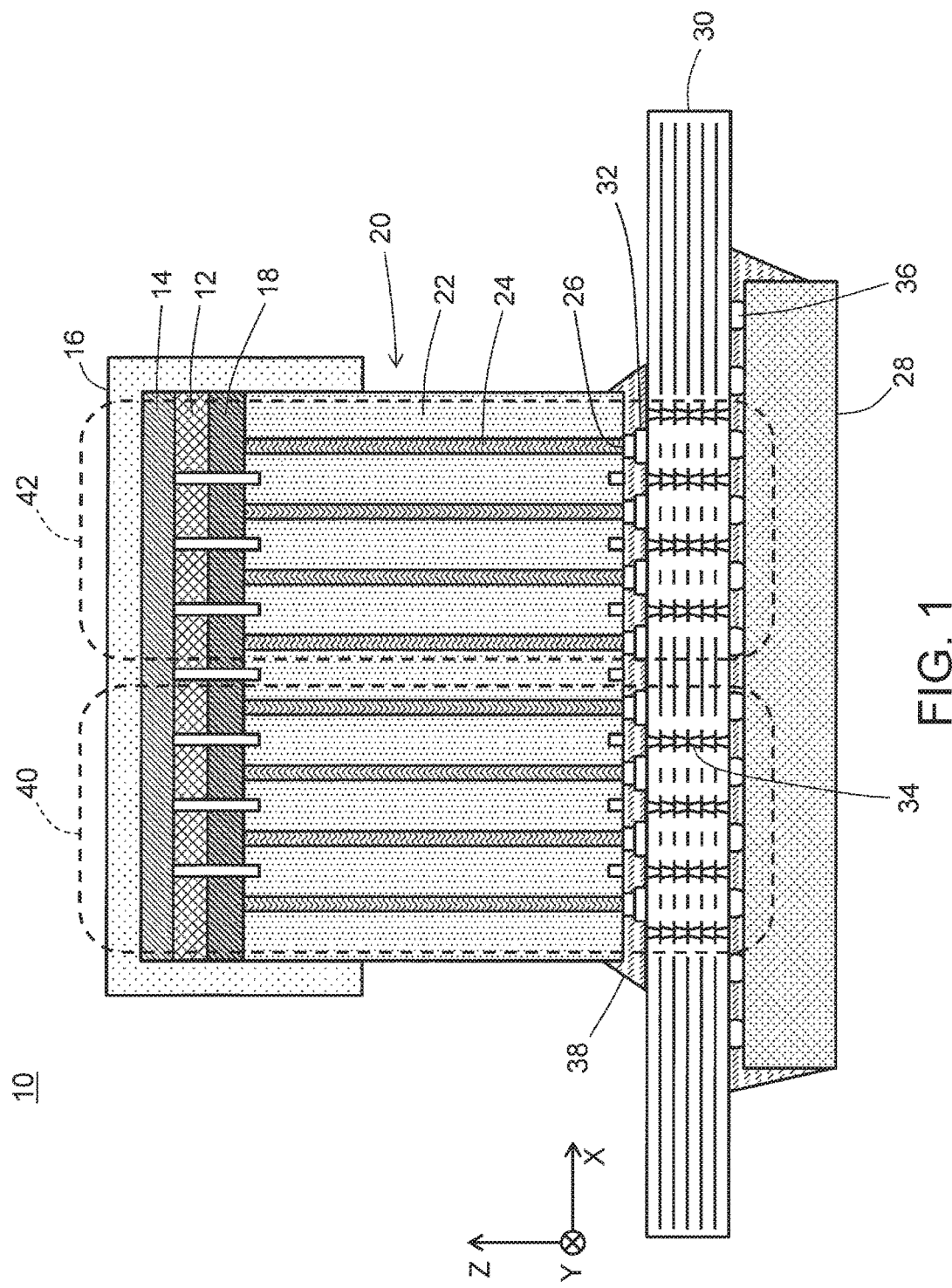
FIG. 1 is a cross sectional view showing an ultrasound probe according to a first embodiment of the present disclosure.

FIG. 1 shows an ultrasound probe according to the first embodiment of the present disclosure. An ultrasound probe 10 is used for an ultrasound diagnosis apparatus. The ultrasound probe 10 is a wave transceiver which transmits and receives ultrasound waves to and from a living body.

The ultrasound probe 10 includes 2D array transducers in which two or more transducers 12 are arranged in two dimensions. The 2D array transducers form transmission beams and reception beams for two-dimensional electric scan. With a two-dimensional scan using ultrasound beams, data for a three-dimensional volume is obtained to form a three-dimensional image based on the obtained data. It should be noted that 1D array transducers in which two or more transducers 12 are linearly aligned may be used in place of the 2D array transducers.

An acoustic matching layer 14 is disposed on an upper surface side (the ultrasound wave transmission/reception side) of the transducers 12. The acoustic matching layer 14 reduces, in a stepwise manner, acoustic impedance from the transducers 12 to a living body so as to acoustically match the transducers 12 and the living body. Although the acoustic matching layer 14 may include only a single layer, the acoustic matching layer 14 may include two or more layers to more smoothly reduce the acoustic impedance to the living body.

A protection layer 16 is disposed to cover the transducers 12. The upper surface of the protection layer 16 is to be placed in contact with a surface of a living body.

A backing 20 is disposed on the rear surface side (on the opposite side of the ultrasound wave transmission/reception side) of the 2D array elements via a hard backing 18. The hard backing 18 is arranged to have higher acoustic impedance than the transducers 12. The hard backing 18 forms a hard rear surface layer such that the transducers 12 and the hard backing 18 unitedly transmit/receive ultrasound waves. The hard backing 18 may be omitted.

A backing 20 is a member for absorbing and dissipating unnecessary ultrasound waves which are emitted from the 217 array transducers towards the rear surface side. The backing 20 is a so called built-in lead array type backing, which mainly includes a backing body 22 and two or more leads 24 embedded therein. The backing body 22 is capable of absorbing or dissipating ultrasound waves. The two or more leads 24 form a lead array. For example, as many of the leads 24 as there are transducers are embedded in the backing body 22. One end of each lead 24 is electrically connected to the corresponding transducer 12. For example, the leads 24 are arranged in the same pattern as the arrangement of the transducers 12, and at the same pitch. Two or more backing terminals 26 which are electrically connected to the other ends of the respective leads 24 are disposed on a lower surface of the backing body 22. The backing terminals 26 are arranged in two dimensions, forming a backing terminal array. For example, as many of the backing terminals 26 as there are transducers are provided. For example, the backing terminals 26 are arranged in the same pattern as the arrangement of the transducers 12, and at the same pitch. The backing terminals 26 are made of a conductive material such as gold (Au).

The ultrasound probe 10 includes an electronic circuit 28. A relay board 30 is disposed as an interposer between the backing 20 and the electronic circuit 28 such that the lead array is electrically connected to the electronic circuit 28 via the relay board 30. For example, the electronic circuit 28 is a control integrated circuit (IC). For example, the electronic circuit 28 is a circuit which generates transmission signals and processes reception signals, in particular, a phasing addition process. Specifically, the electronic circuit 28 may include at least one of a receiver circuit which processes as many reception signals as there are transducers by applying, in units of certain groups, the phasing addition process to generate a certain number of reception signals, and a transmitter circuit which generates as many transmission drive signals as there are transducers based on a single or a certain number of transmission signals.

The relay board 30 is a substrate used to electrically connect the transducers 12 and the electronic circuit 28. The relay board 30 may be, for example, a multilayer substrate in which two or more substrates are stacked. The relay board 30 may be capable of switching the connection between a terminal (an electrode pad) on the electronic circuit 28 and the transducers 12. The relay board 30 is made of an epoxy resin or other resin material.

The relay board 30 includes two or more electrodes corresponding to the backing terminals 26. The electrodes are arranged in two-dimensions, forming an electrode array. Each electrode includes a board terminal 32, a via 34 (or a through-hole), and a conductive channel which electrically connects the board terminal 32 and the via 34. For example, as many of the electrodes as there are transducers are disposed. In other words, the board terminals 32, the vias 34, and the conductive channels are respectively provided as many in number as the number of transducers. The board terminals 32 are arranged in the same pattern as the arrangement of the backing terminals 26, and at the same pitch. The board terminal 32 are provided on an upper surface of the relay board 30 and electrically connected to the corresponding backing terminals 26. The board terminals 32 may be, for example, bump-shaped conductive members formed by soldering or the like. For example, the backing terminals 26 and the board terminals 32 may be connected using silver paste or other materials. The vias 34 may be internal wiring within a substrate laid from the upper surface to the lower surface of the relay board 30 such that the vias 34 are electrically connected to the terminals 36 on the electronic circuit 28 on the lower surface of the relay board 30. The electrodes are described below with reference to FIG. 2A and the subsequent drawings.

Two or more terminals 36 are disposed on the upper surface of the electronic circuit 28. The terminals 36 are arranged in two-dimensions, forming a terminal array. The terminals 36 are electrically connected to the corresponding vias 34. The terminals 36 are, for example, bump-shaped conductive members formed by soldering or the like.

The backing 20, the electronic circuit 28, and the relay board 30 are attached to each other by adhesive 38 such as an epoxy resin.

In a continuous wave Doppler mode (CW mode), the transducers 12 (2D array transducers) are divided into a transmitter group and a receiver group. The transmitter group includes two or more transmitter transducers 12 (transmitter transducer array), whereas the receiver group includes two or more receiver transducers 12 (receiver transducer array). For example, the transducers 12 are equally divided into the transmitter group and the receiver group. For example, a transmitter group 40 includes a transmitter transducer array, two or more transmitter leads 24 (transmitter lead sub-array), 25 two or more transmitter backing terminals 26 (transmitter backing terminal sub-array), and two or more transmitter electrodes (transmitter electrode array). A receiver group 42 includes a receiver transducer array, two or more receiver leads 24 (receiver lead sub-array), two or more receiver backing terminals 26 (reception backing terminal sub-array), and two or more receiver electrodes (receiver electrode array).

The transmitter lead array is an example of a "first lead sub-array", the transmitter backing terminal sub-array is an example of a "first backing terminal sub-array", and the transmitter electrode array is an example of a "first electrode array". Further, the reception lead array is an example of a "second lead sub-array", the reception backing terminal sub-array is an example of a "second backing terminal sub-array", and the receiver electrode array is an example of a "second electrode array".

Figure 2:
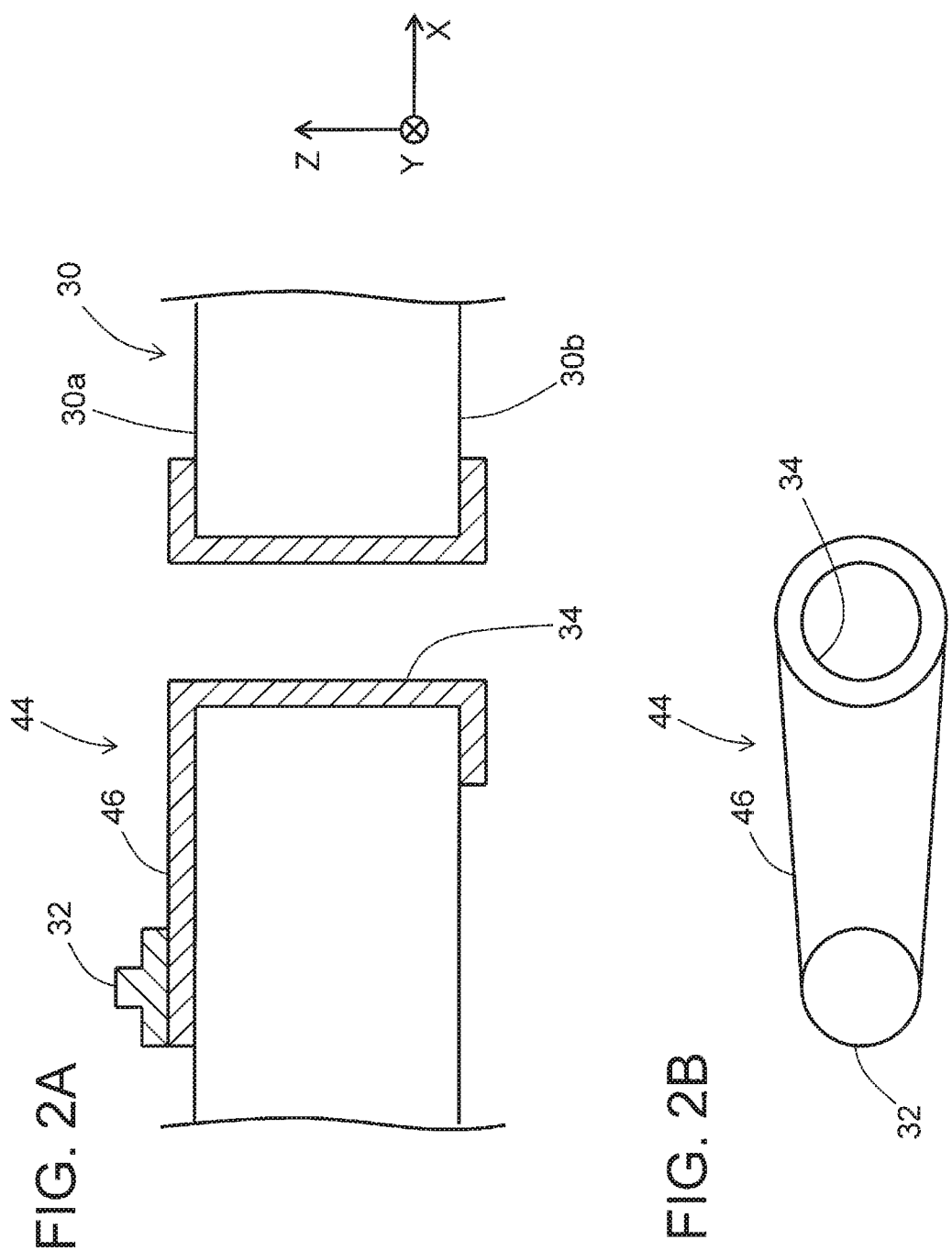
FIG. 2A is a diagram showing a structure of a relay board where an electrode is located.
FIG. 2B is a diagram showing a structure of the electrode at the relay board.

The electrodes disposed on the relay board 30 are described in detail below. FIGS. 2A and 2B show an example of the electrode. FIG. 2A is an enlarged cross-sectional view of the relay board 30 and an electrode 44. FIG. 2B is a drawing showing an XY plane. FIG. 2B shows the electrodes 44 viewed from an upper surface 30a side of the relay board 30.

The board terminals 32 are disposed on the upper surface 30a of the relay board 30. The board terminals 32 are a conductive member such as metal having a concaved bump shape and are electrically connected to the backing terminals 26. The vias 34 are shifted from the board terminal 32. The vias 34 are formed from the upper surface 30a to the lower surface 30b of the relay board 30. Each via 34 includes a conductive member such as metal. The conductive member on the lower surface 30b of the relay board 30 is electrically connected to the terminal 36 on the electronic circuit 28. Each board terminal 32 and the corresponding via 34 are electrically connected via a conductive channel 46. The conductive channel 46 is a conductive member such as metal. Each electrode 44 includes the board terminal 32, the via 34, and the conductive channel 46. As many of the electrodes 44 as there are transducers are provided on the relay board 30, forming an electrode array. In each electrode 44, a path from the board terminal 32 to the via 34 is defined as, for example, a position vector. When the relay board 30 is a multi-layer substrate, the via 34 is formed on each of the substrates such that the upper surface and the lower surface of the relay board 30 are electrically connected by a conductive material in the via 34.

Figure 3:
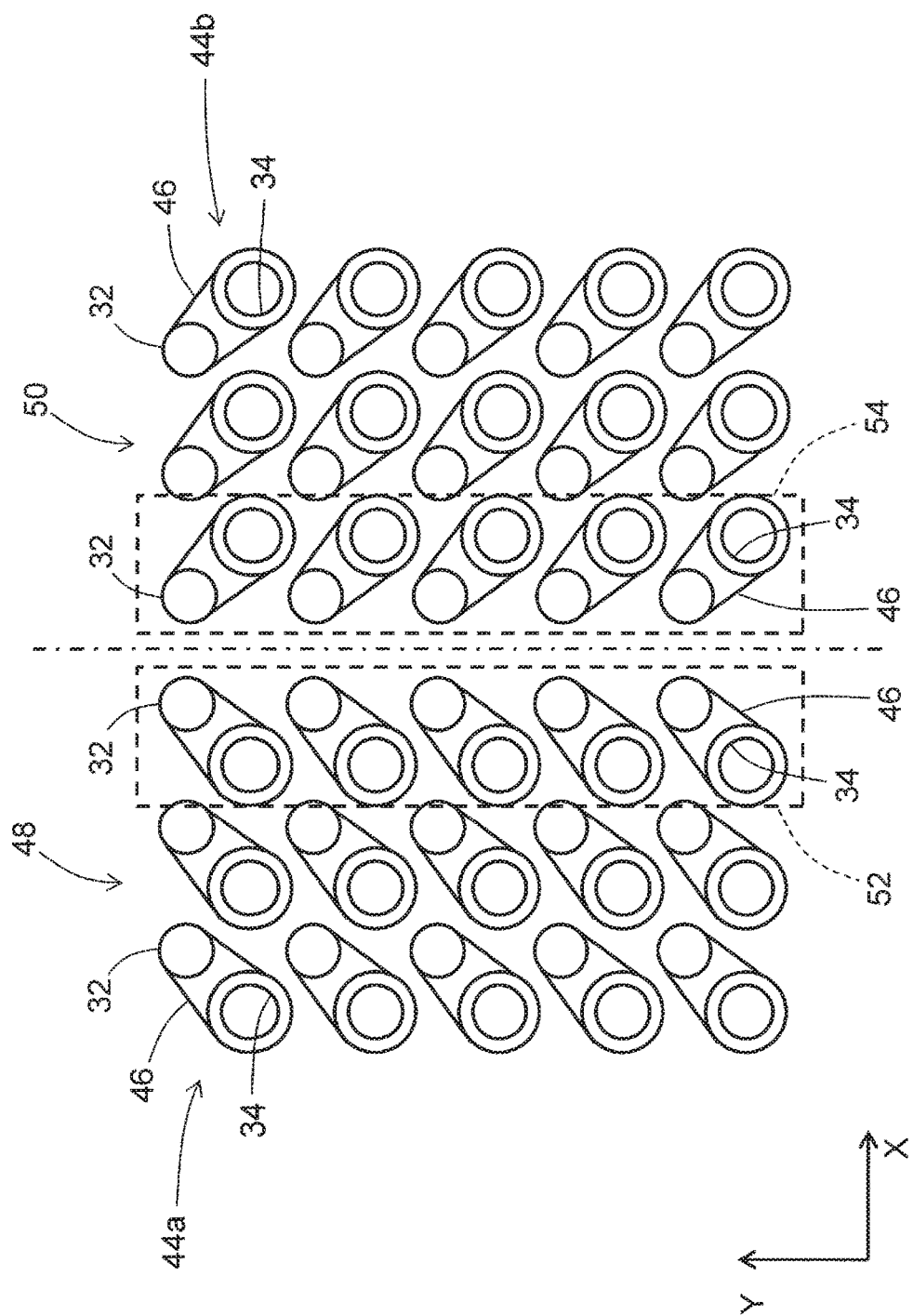
FIG. 3 is a plan view showing a layout of an electrode array according to the first embodiment.

The electrode array is described in detail below. FIG. 3 shows a layout of the electrode array according to a first embodiment. FIG. 3 is a drawing showing an XY plane, viewing the electrode array from above (from the upper surface 30*a* side of the relay board 30).

The two or more electrodes 44 are arranged in two-dimensions, forming the electrode array. The two or more board terminals 32 are arranged at the same pitch as the backing terminals 26. The board terminals 32 are arranged in two-dimensions, forming a board terminal array corresponding to the backing terminal array.

In the CW mode, the electrode array is divided into a transmitter electrode array 48 and a receiver electrode array 50. For example, the electrode array is divided at the center (shown by the dash-dot line) to the transmitter electrode array 48 and the receiver electrode array 50. The electrodes 44 for transmission are referred to as "transmitter electrodes 44*a*", whereas the electrodes 44 for reception are referred to as "receiver electrodes 44*b*". The transmitter electrode array 48 includes two or more transmitter electrodes 44*a*, whereas the receiver electrode array 50 includes two or more receiver electrodes 44*b*. The transmitter electrode array 48 is a group of electrodes in an area responsive to a transmission side in the CW mode, whereas the receiver electrode array 50 is a group of electrodes in an area responsive to a reception side in the CW mode. In other words, the transmitter electrode array 48 is a group of electrodes responsive to the transmitter transducer array, whereas the receiver electrode array 50 is a group of electrodes responsive to the receiver transducer array.

The transmitter electrode array 48 is an example of a "first electrode array", two or more board terminals 32 included in the transmitter electrode array 48 are an example of a "first board terminal sub-array", the two or more vias 34 included in the transmitter electrode array 48 are an example of a "first via sub-array", and the two or more conductive channels 46 included in the transmitter electrode array 48 are an example of a "first conductive channel sub-array". Further, the receiver electrode array 50 is an example of a "second electrode array", the two or more board terminal 32 included in the receiver electrode array 50 are an example of a "second board terminal sub-array", the two or more vias 34 included in the receiver electrode array 50 are an example of a "second via sub-array", and the two or more conductive channels 46 included in the receiver electrode array 50 are an example of a "second conductive channel sub-array".

The two or more board terminals 32 (the first board terminal sub-array) included in the transmitter electrode array 48 are electrically connected to the transmitter backing terminal sub-array (the first backing terminal sub-array) in the backing terminal array. Similarly, the two or more board terminals 32 (the second board terminal sub-array) included in the receiver electrode array 50 are electrically connected to the receiver backing terminal sub-array (the second backing terminal sub-array) in the receiver backing terminal array.

As shown in FIG. 3, the two or more vias 34 (the first via sub-array) included in the transmitter electrode array 48 have a two-dimensional arrangement which is identical to the two-dimensional arrangement of the board terminals 32 (the first board terminal sub-array) included in the transmitter electrode array 48 shifted in parallel in a first direction. The first direction is a direction away from the border in the transmitter electrode array 48. Similarly, the two or more vias 34 (the second via sub-array) included in the receiver electrode array 50 have a two-dimensional arrangement which is identical to the two-dimensional arrangement of the board terminals 32 (the second board terminal sub-array) included in the receiver electrode array 50 shifted in parallel in a second direction. The second direction is a direction away from the border in the receiver electrode array 50. As an example, the first and second directions are oblique to the direction orthogonal to the boundary. In this way, the layouts of the electrodes 44 are different between the transmitter electrode array 48 and the receiver electrode array 50. Although the vias 34 for the two arrays are disposed away ("shifted") from the board terminals 32, the shift pattern is different between the transmitter electrode array 48 and the receiver electrode array 50. More specifically, a "positional vector" defined as a path from each board terminal 32 to the corresponding via 34 is different between them.

For example, in the transmitter electrode array 48 and the receiver electrode array 50 on respective sides of the dash-dot center line, each transmitter electrode 44*a* and each receiver electrode 44*b* are arranged such that each board terminal 32 is disposed on an inner side (on the center side), whereas each via 34 is positioned on the outer side. In the example shown in FIG. 3, each board terminal 32 is disposed obliquely upward on the right, whereas each via 34 is disposed obliquely downward on the left in the transmitter electrode array 48. In the receiver electrode array 50, each board terminal 32 is disposed obliquely upward on the left, whereas each via 34 is disposed obliquely downward on the right. In other words, the vias 34 are formed such that the vias 34 in the transmitter electrode array 48 and the vias 34 in the receiver electrode array 50 are directed away from each other. As an example, by using an X axis and a Y axis as references, the path (shift vector) from each board terminal 32 to the corresponding via 34 in the transmitter electrode array 48 is tilted obliquely downward 45° on the left, whereas in the receiver electrode array 50, the path is tilted obliquely downward 45° on the right. This tilting angle is merely an example. Other tilting angles may be applied. It should be noted that oblique paths (shift vector) can reduce the space for disposing the electrodes 44. In this way, the size of the ultrasound probe 10 can be reduced. The 45° tilting angle can optimize the arranging conditions of the electrodes 44, further reducing space.

It is also possible that some or all of the shift patterns of the electrodes 44 may be different between the transmitter electrode array 48 and the receiver electrode array 50. For example, the transmitter electrodes 44*a* and the receiver electrodes 44*b* may have shift patterns such that the board terminals 32 in the transmitter electrode array 48 in the column (transmitter electrode column 52) closest to the receiver electrode array 50 and the board terminal 32 in the receiver electrode array 50 in the column (receiver electrode column 54) closest to the transmitter electrode array 48 are disposed on the inner side with the vias 34 on the outer side, whereas the other electrodes 44 may have an identical shift pattern. In summary, the shift patterns may be arranged such that the board terminals 32 are disposed on the inner side and the vias 34 are disposed on the outer side in the transmitter electrode column 52 and the receiver electrode column 54, both of which are closest to the center line shown by the broken lines.

The transmitter electrode column 52 and the receiver electrode column 54 may be columns of unused electrodes, which are not used for transmitting and receiving ultrasound waves. In this case, the electrodes 44 may have an identical shift pattern in the transmitter electrode column 52 and the receiver electrode column 54.

As described above, in the first embodiment, the layouts (shift patterns) of the electrodes 44 are different between the transmitter electrode array 48 and the receiver electrode array 50. In this way, it becomes possible to prevent or reduce electrical crosstalk in comparison with arranging the electrodes 44 identically between these arrays. For example, the transmitter electrodes 44a and the receiver electrodes 44b are arranged such that the board terminal 32 are disposed on the inner side (on the center side) and the vias 34 are disposed on the outer side in the transmitter electrode array 48 and the receiver electrode array 50. In this way, in comparison with arranging the electrodes 44 in an identical layout, the distance between the vias 34 and the distance between the board terminal 32 and the vias 34 become longer between the transmitter electrode column 52 and the receiver electrode column 54. In other words, the distance between the vias 34 in the transmitter electrode column 52 and the vias 34 in the receiver electrode column 54 becomes longer. Further, the distance between the board terminals 32 in the transmitter electrode column 52 and the vias 34 in the receiver electrode column 54 becomes longer. Similarly, the distance between the board terminal 32 in the receiver electrode column 54 and the vias 34 in the transmitter electrode column 52 becomes longer. Accordingly, the following electrical crosstalk can be prevented or reduced: electrical crosstalk between the vias 34 in the transmitter electrode column 52 and the vias 34 in the receiver electrode column 54; electrical crosstalk between the board terminal 32 in the transmitter electrode column 52 and the vias 34 in the receiver electrode column 54; and electrical crosstalk between the vias 34 in the transmitter electrode column 52 and the board terminal 32 in the receiver electrode column 54. Possible causes of the electrical crosstalk are, for example, a capacitive coupling and an inductive coupling between electrodes or signal lines which are arranged in two dimensions. Such couplings can be prevented or reduced according to the first embodiment, because of the longer distances between the members (the board terminals 32 and the vias 34) between the transmitter electrode column 52 and the receiver electrode column 54. This can prevent or reduce the electrical crosstalk.

COMPARATIVE EXAMPLE

Figure 4:
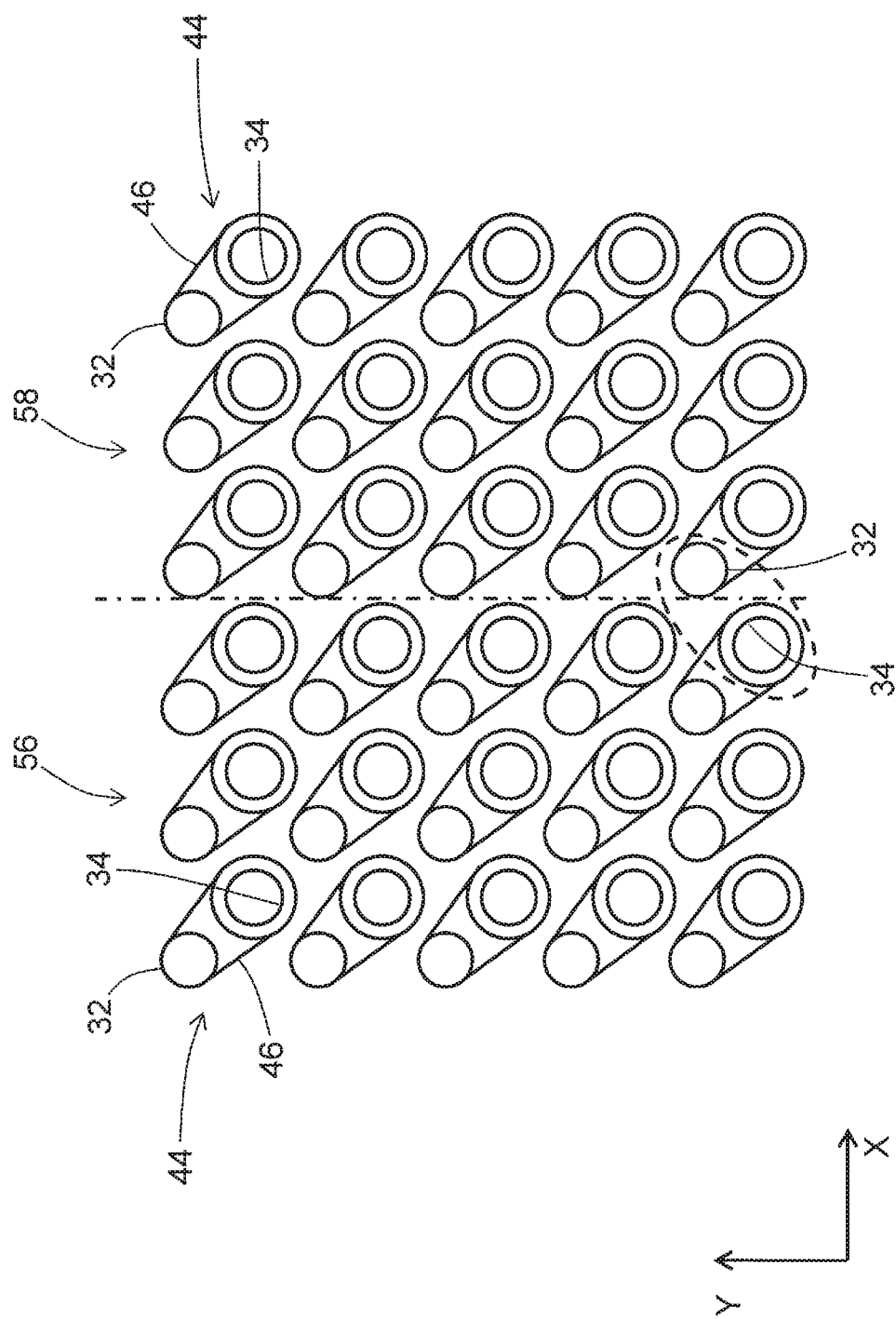
FIG. 4 is a plan view showing a layout of an electrode array according to a comparative example.

A comparative example is described below. FIG. 4 shows a layout of an electrode array according to a comparative example. FIG. 4 shows an XY plane, viewing the electrode array from the above.

Also in this comparative example, two or more electrodes 44 are arranged in two-dimensions, forming an electrode array. The structure of each electrode 44 itself is identical to the electrode 44 according to the first embodiment. The board terminals 32 are arranged at the same pitch as the backing terminals 26.

In the CW mode, the electrode array is divided into a transmitter electrode array 56 and a receiver electrode array 58. For example, the electrode array is divided at the center (shown by the dash-dot line) to the transmitter electrode array 56 and the receiver electrode array 58. The transmitter electrode array 56 is a group of electrodes responsive to the transmitter transducer array, whereas the receiver electrode array 58 is a group of electrodes responsive to the receiver transducer array.

In order to maintain space to place the electrodes 44, each electrode 44 is arranged such that the path (shift vector) from the board terminal 32 to the via 34 is tilted 45° with respect to the X axis or the Y axis. In this comparative example, all the electrodes 44 are arranged in the same layout. Specifically, the layout of the electrodes 44 in the transmitter electrode array 56 and the layout of the electrodes 44 in the receiver electrode array 58 are identical such that the shift patterns of all the electrodes 44 are identical. In the example shown in FIG. 4, each board terminal 32 is disposed obliquely upward on the left, whereas the corresponding via 34 is disposed obliquely downward on the right in all the electrodes 44.

When the electrodes 44 are obliquely placed, the distance between the board terminal 32 and the via 34 in the adjacent two electrodes 44 becomes shorter in comparison with the electrodes 44 arranged along the X axis or the Y axis. When the board terminal 32 and the vias 34 are arranged at the same pitch as the leads 24, the distance between the board terminal 32 and the via 34 becomes shorter than the pitch. In this comparative example, the layouts of the electrodes 44 in the transmitter electrode array 56 and the receiver electrode array 58 do not differ from each other such that all the electrodes 44 are obliquely arranged in the same direction. In this case, because of the short distances between the board terminals 32 and the vias 34 between the electrodes 44 in the transmitter electrode array 56 in the column closest to the receiver electrode array 58 and the electrodes 44 in the receiver electrode array 58 in the column closest to the transmitter electrode array 56, electric crosstalk becomes more likely to occur at that portion. For example, electric crosstalk becomes more likely to occur between the board terminal 32 on the transmitter electrode side and the via 34 on the receiver electrode side which are encircled by a broken line. Similarly, electrical crosstalk may occur between the vias 34 in the transmitter electrode array 56 in the column closest to the receiver electrode array 58 and the vias 34 in the receiver electrode array 58 in the column closest to the transmitter electrode array 56 when the distance between the vias 34 becomes short depending on the pitch. In particular, because the vias 34 are formed from the upper surface to the lower surface of the relay board 30, the vias 34 may have a long length. The longer the length of the via 34, the more likely it becomes for electric crosstalk to occur between the via 34 on the transmitter electrode side and the via 34 on the receiver electrode side. The pitch is, for example, about 50 μm, at which electric crosstalk becomes likely to occur between the transmitter electrode side and the receiver electrode side.

In comparison with this comparative example, the first embodiment can achieve a longer distance than the comparative example between the vias 34 and between the board terminals 32 and the vias 34, between the transmitter electrode column 52 and the receiver electrode column 54. This can prevent or reduce the occurrence of electrical crosstalk between the transmitter electrode side and the receiver electrode side.

Second Embodiment

Figure 5:
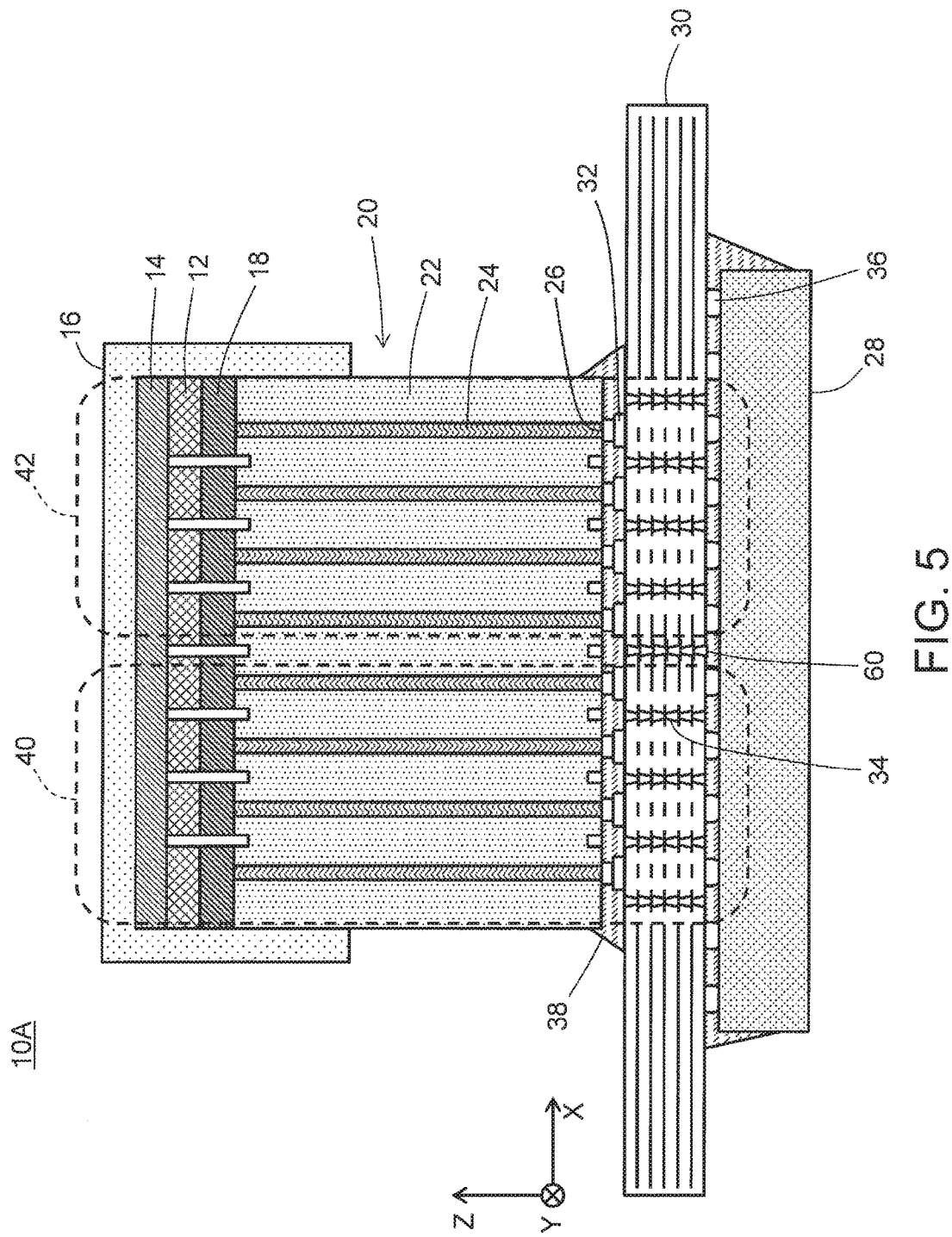
FIG. 5 is a cross sectional view showing an ultrasound probe according to a second embodiment of the present disclosure.

An ultrasound probe according to a second embodiment of the present disclosure is described below. FIG. 5 shows an ultrasound probe 10A according to the second embodiment.

The ultrasound probe 10A includes ground electrodes 60 on the relay board 30. The structure of the ultrasound probe 10A is identical to the ultrasound probe 10 according to the first embodiment except for the ground electrodes 60. The ground electrodes 60 are, for example, vias or through-holes for grounding. The ground electrodes 60 are provided between a transmitter group 40 and a receiver group 42.

Figure 6:
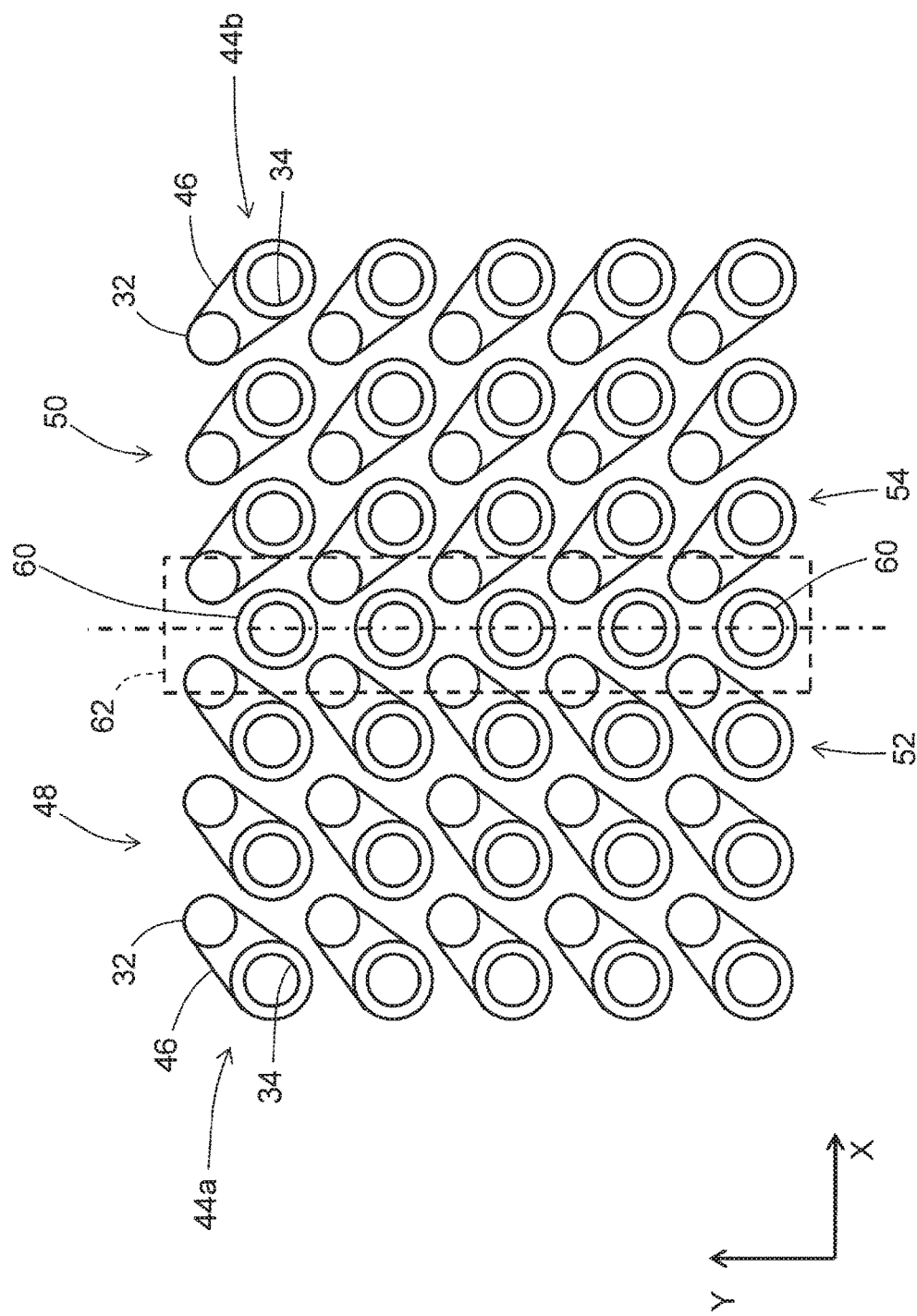
FIG. 6 is a plan view showing a layout of an electrode array according to the second embodiment.

An electrode array disposed on a relay board 30 is described in detail below. FIG. 6 shows a layout of the electrode array according to the second embodiment. FIG. 6 shows an XY plane, viewing the electrode array from above (from the upper surface 30a side of the relay board 30).

Similarly to the first embodiment, two or more electrodes 44 are arranged in two-dimensions, forming an electrode array. In the CW mode, the electrode array is divided into a transmitter electrode array 48 and a receiver electrode array 50. The transmitter electrodes 44a and the receiver electrodes 44b have an identical shift pattern to the first embodiment.

In the second embodiment, the ground electrodes 60 are disposed in a space zone between the transmitter electrode column 52 and the receiver electrode column 54. For example, two or more round electrodes 60 are linearly aligned to form a ground electrode column 62.

A shield effect can be obtained at that portion by providing the ground electrode column 62 between the transmitter electrode column 52 and the receiver electrode column 54 as described above. This can further reduce the electrical crosstalk between the transmitter electrode column 52 and the receiver electrode column 54.

Third Embodiment

Figure 7:
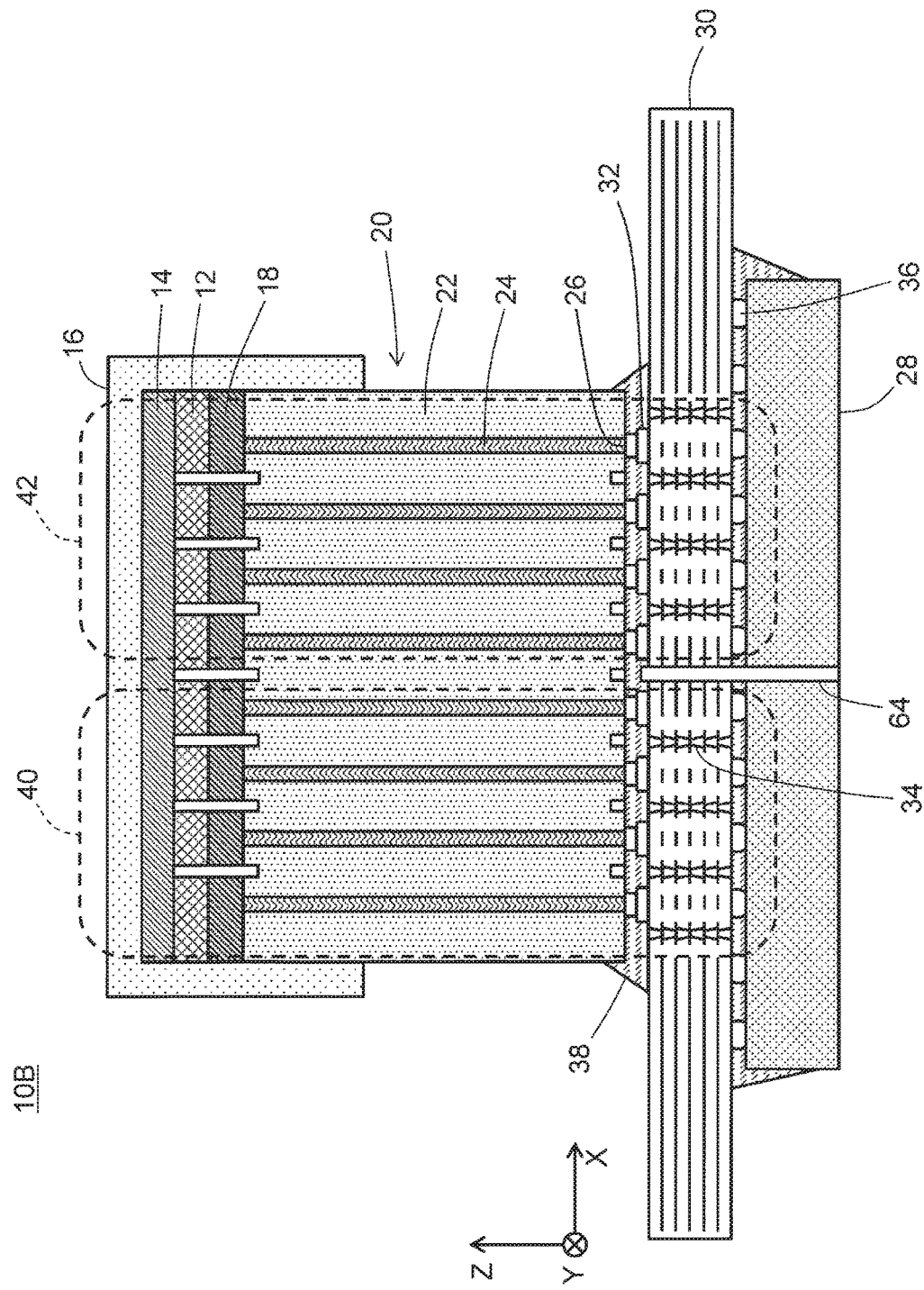
FIG. 7 is a cross sectional view showing an ultrasound probe according to a third embodiment of the present disclosure.

An ultrasound probe according to a third embodiment of the present disclosure is described below. FIG. 7 shows an ultrasound probe 10B according to the third embodiment.

In the ultrasound probe 10B, an acoustic separation groove 64 is formed on the relay board 30. The acoustic separation groove 64 may be formed only on the relay board 30 or also on the electronic, circuit 28 as shown in FIG. 7. The structure of the ultrasound probe 10B is identical to the ultrasound probe 10 according to the first embodiment except for the acoustic separation groove 64. The acoustic separation groove 64 may be formed by a dicing or other process. The acoustic separation groove 64 is formed between the transmitter group 40 and the receiver group 42 on the relay board 30 to acoustically separate between the transmitter group 40 and the receiver group 42.

Figure 8:
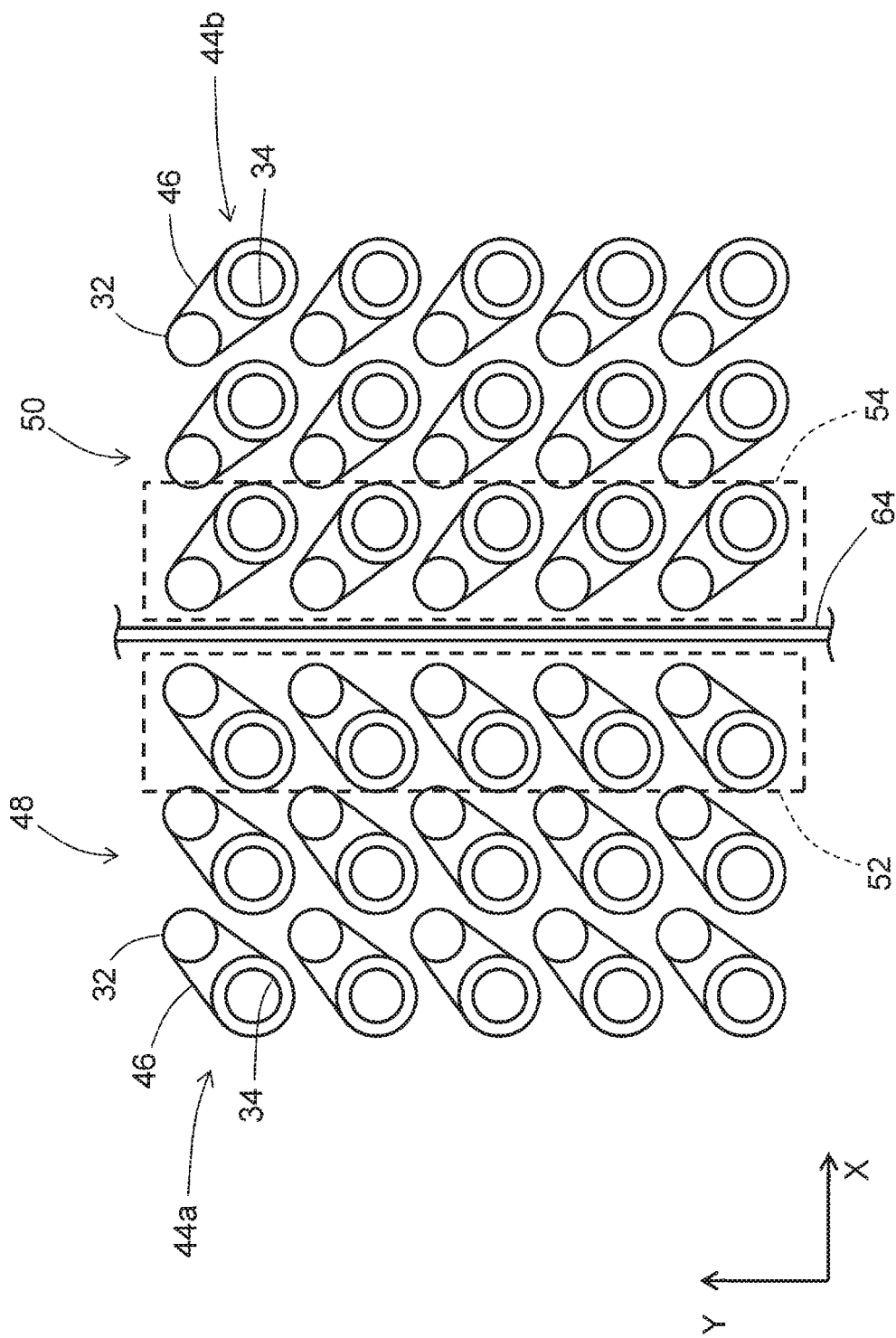
FIG. 8 is a plan view showing a layout of an electrode array according to the third embodiment.

An electrode array disposed on a relay board 30 is described in detail below. FIG. 8 shows a layout of the electrode array according to the third embodiment. FIG. 8 shows an XY plane, viewing the electrode array from above (from the upper surface 30a side of the relay board 30).

Similarly to the first embodiment, two or more electrodes 44 are arranged in two dimensions, forming an electrode array. In the CW mode, the electrode array is divided into a transmitter electrode array 48 and a receiver electrode array 50. The transmitter electrodes 44a and the receiver electrodes 44b both have identical shift patterns to those according to the first embodiment.

In the third embodiment, a linear acoustic separation groove 64 is formed along the Y axis in a space zone between the transmitter electrode column 52 and the receiver electrode column 54. Because this physically separates between the transmitter electrode array 48 and the receiver electrode array 50, acoustic crosstalk between the transmitter electrode array 48 and the receiver electrode array 50 can be prevented or reduced. A possible cause of the acoustic crosstalk is that ultrasound waves propagate through a continuous member, and escape into an adjacent element. When the relay board 30 includes a continuous member, ultrasound waves propagate on the relay board 30 through the transmitter electrode array 48 and the receiver electrode array 50, causing the acoustic crosstalk. Because the transmitter electrode array 48 and the receiver electrode array 50 are physically separated by the acoustic separation groove 64 according to the third embodiment, the propagation of the ultrasound waves is blocked at that portion. In other words, because the continuity of the relay board 30 is cut by the acoustic separation groove 64, the propagation of the ultrasound waves is blocked. In this way, the acoustic crosstalk between the transmitter electrode array 48 and the receiver electrode array 50 can be prevented or reduced. According to the third embodiment, not only the electric crosstalk but also the acoustic crosstalk can be prevented or reduced.

Fourth Embodiment

Figure 9:
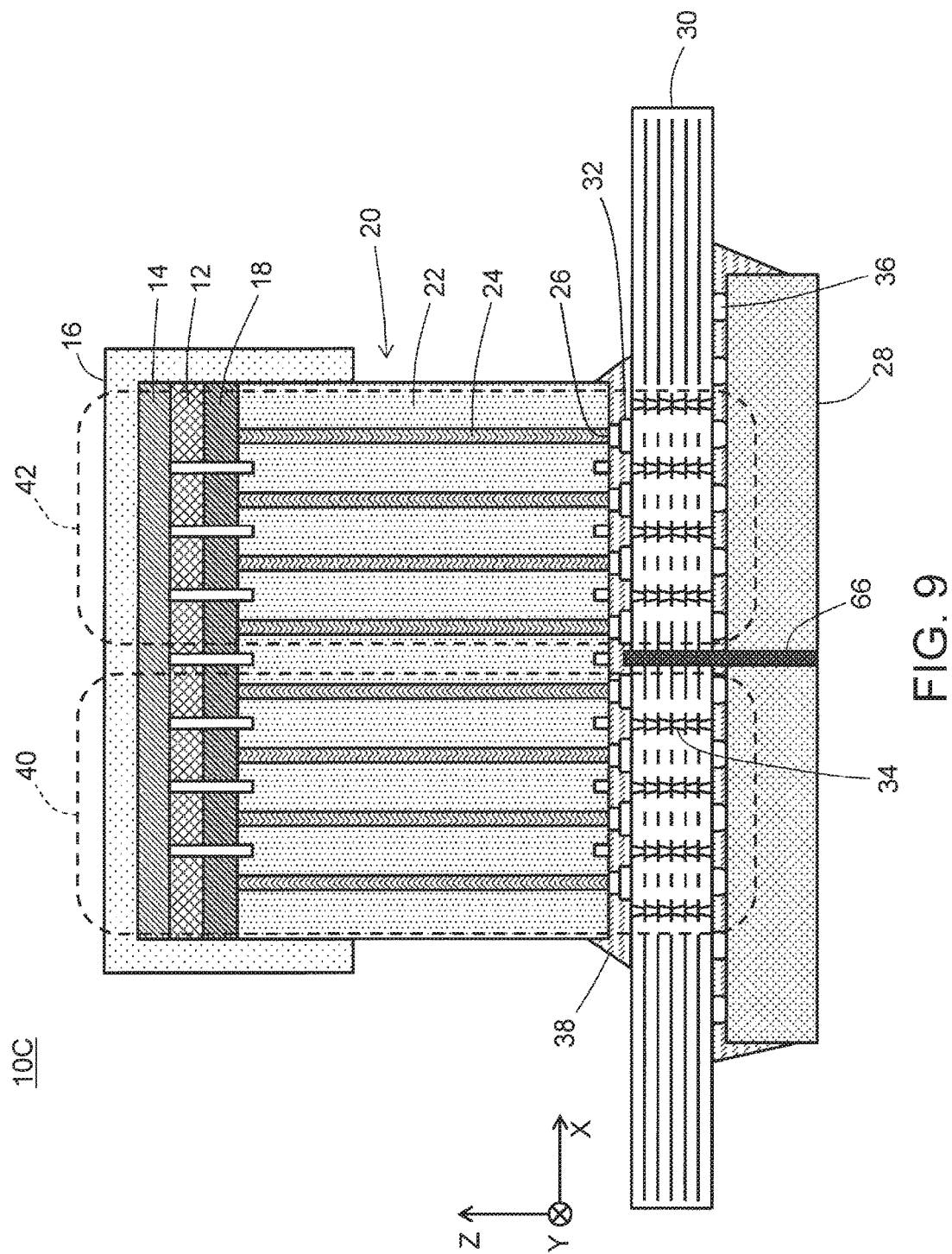
FIG. 9 is a cross sectional view showing an ultrasound probe according to a fourth embodiment of the present disclosure.

An ultrasound probe according to a fourth embodiment of the present disclosure is described below. FIG. 9 shows an ultrasound probe 10C according to the fourth embodiment.

Similarly to the ultrasound probe 10B according to the third embodiment, the ultrasound probe 10C includes an acoustic separation groove formed on the relay board 30. In the fourth embodiment, the acoustic separation groove is filled with an acoustic separation material 66. The structure of the ultrasound probe 10C is identical to the ultrasound probe 10 according to the first embodiment except for the acoustic separation material 66. The acoustic separation material 66 is disposed between the transmitter group 40 and the receiver group 42 on the relay board 30 to acoustically separate between the transmitter group 40 and the receiver group 42. The acoustic separation material 66 may be provided only on the relay board 30 or also on the electronic circuit 28 as shown in FIG. 9.

Figure 10:
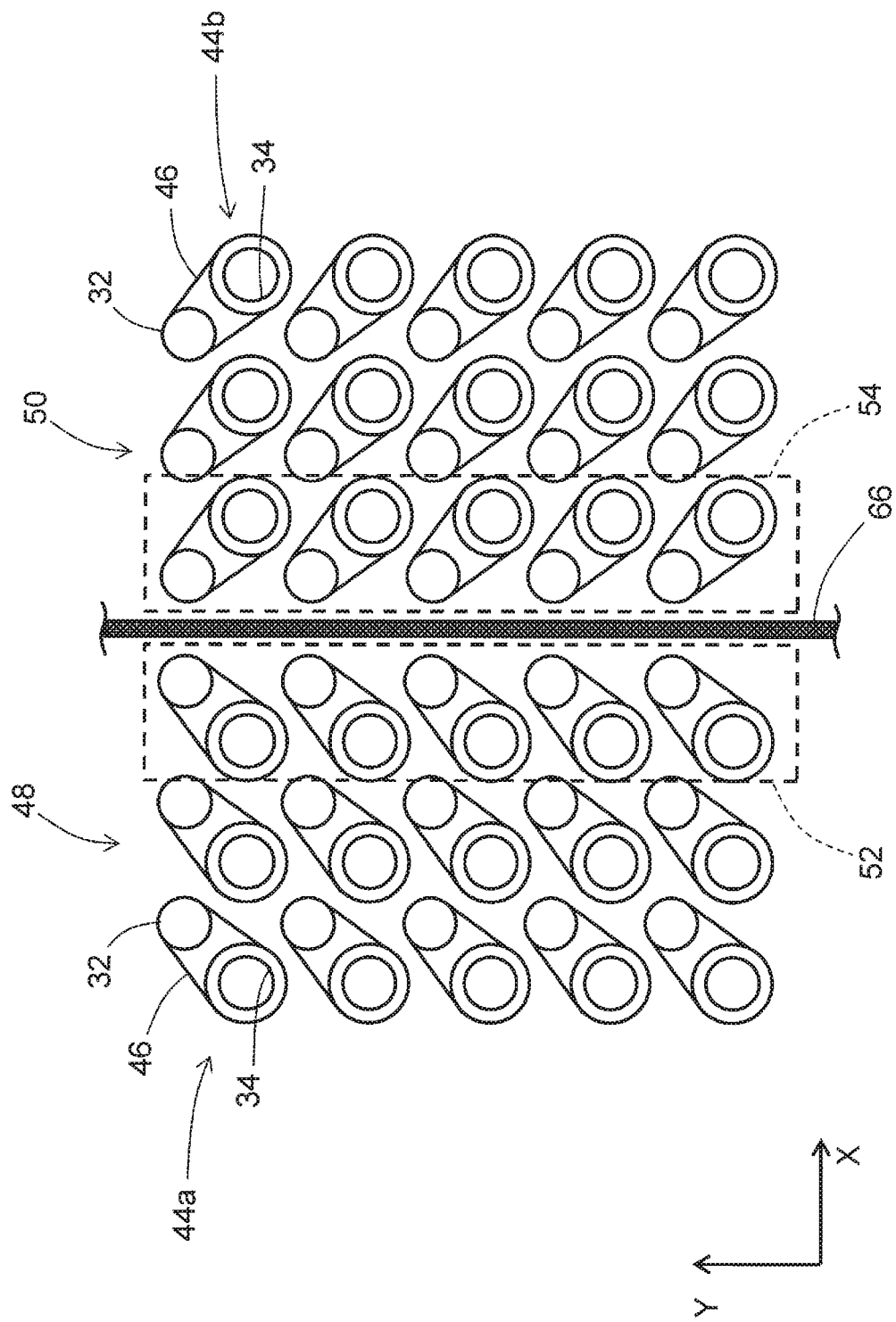
FIG. 10 is a plan view showing a layout of an electrode array according to the fourth embodiment.

The electrode array disposed on the relay board 30 is described in detail below. FIG. 10 shows a layout of the electrode array according to the fourth embodiment. FIG. 10 shows an XY plane, viewing the electrode array from above (from the upper surface 30a side of the relay board 30).

In the fourth embodiment, a linear acoustic separation groove is provided between the transmitter electrode column 52 and the receiver electrode column 54 similarly to the third embodiment, and filled with the acoustic separation material 66. The acoustic separation material 66 is made of a resin or other material different from the relay board 30. The acoustic separation material 66 physically separates between the transmitter electrode array 48 and the receiver electrode array 50, further preventing or reducing the acoustic crosstalk between the transmitter electrode array 48 and the receiver electrode array 50. In other words, the continuity of the relay board 30 is cut by the acoustic separation material 66 such that the propagation of the ultrasound waves is blocked. As a result, the acoustic crosstalk between the transmitter electrode array 48 and the receiver electrode array 50 is prevented or reduced. According to the fourth embodiment, not only the electric crosstalk but also the acoustic crosstalk can be prevented or reduced.

Fifth Embodiment

Figure 11:
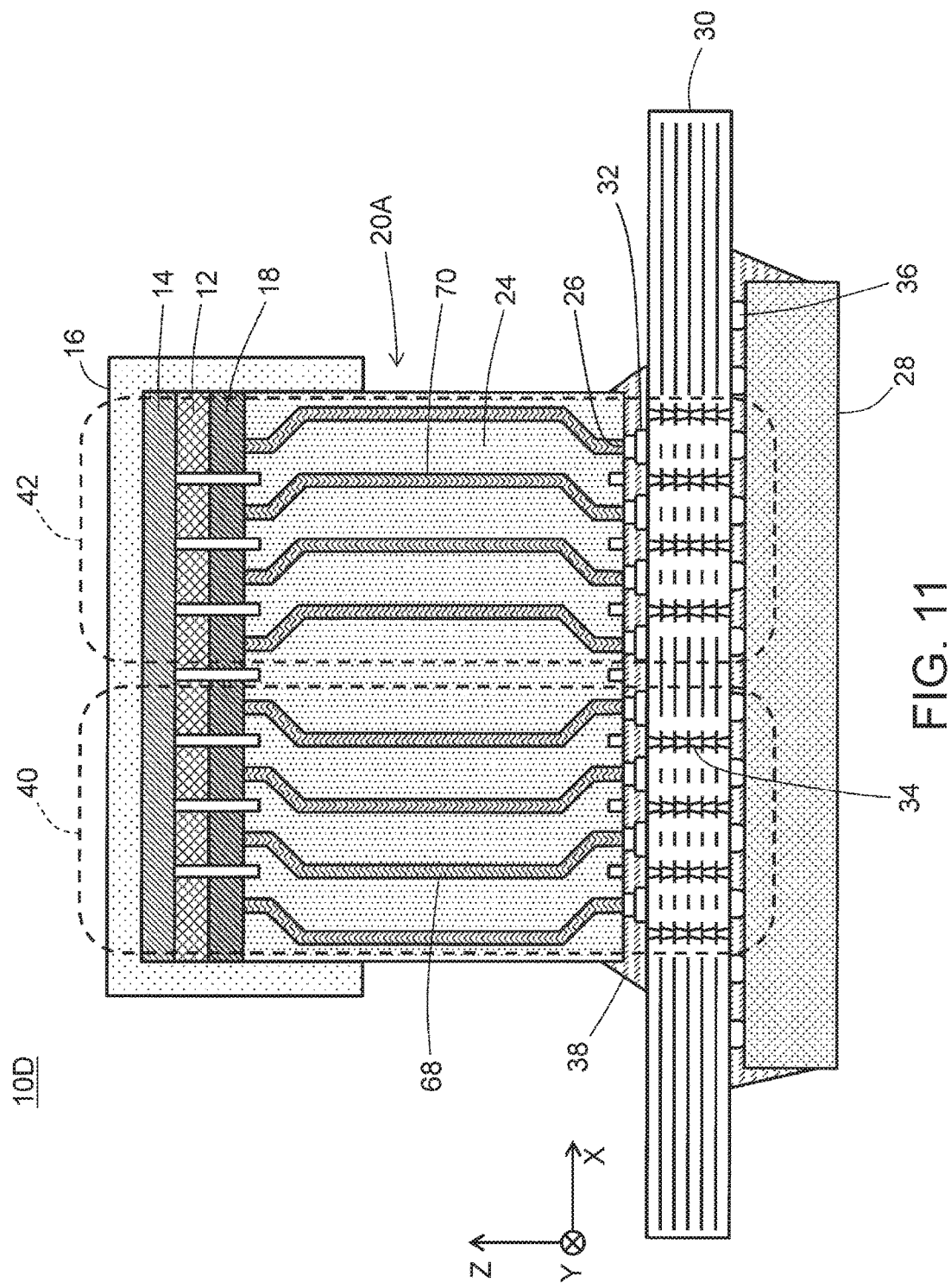
FIG. 11 is a cross sectional view showing an ultrasound probe according to a fifth embodiment.

An ultrasound probe according to a fifth embodiment of the present disclosure is described below. FIG. 11 shows an ultrasound probe 10D according to the fifth embodiment.

The ultrasound probe 10D includes a backing 20A in place of the backing 20 according to the first embodiment. The structure of the ultrasound probe 10D is identical to the ultrasound probe 10 according to the first embodiment except for the backing 20A.

The backing 20A is a so called built-in lead array type backing, which mainly includes a backing body 22 and two or more leads 68, 70 embedded therein. The leads 68 are leads for transmission belonging to the transmitter group 40, whereas the leads 70 are leads for reception belonging to the receiver group 42. Two or more leads 68 form a transmitter lead sub-array, whereas two or more leads 70 form a receiver lead sub-array The transmitter lead sub-array is an example of a "first lead sub-array", whereas the receiver lead sub-array is an example of a "second lead sub-array". In the lead array, the transmitter lead sub-array and the receiver lead sub-array are arranged away from each other in the horizontal direction. In this way, electrical crosstalk between the transmitter lead sub-array and the receiver lead sub-array can also be prevented or reduced in the lead array.

The transmitter lead sub-array and the receiver lead sub-array may be arranged away from each other in the horizontal direction in the ultrasound probes 10A, 10B, and IOC by combining the fifth embodiment with the second, third, and fourth embodiments.

Sixth Embodiment

Figure 12:
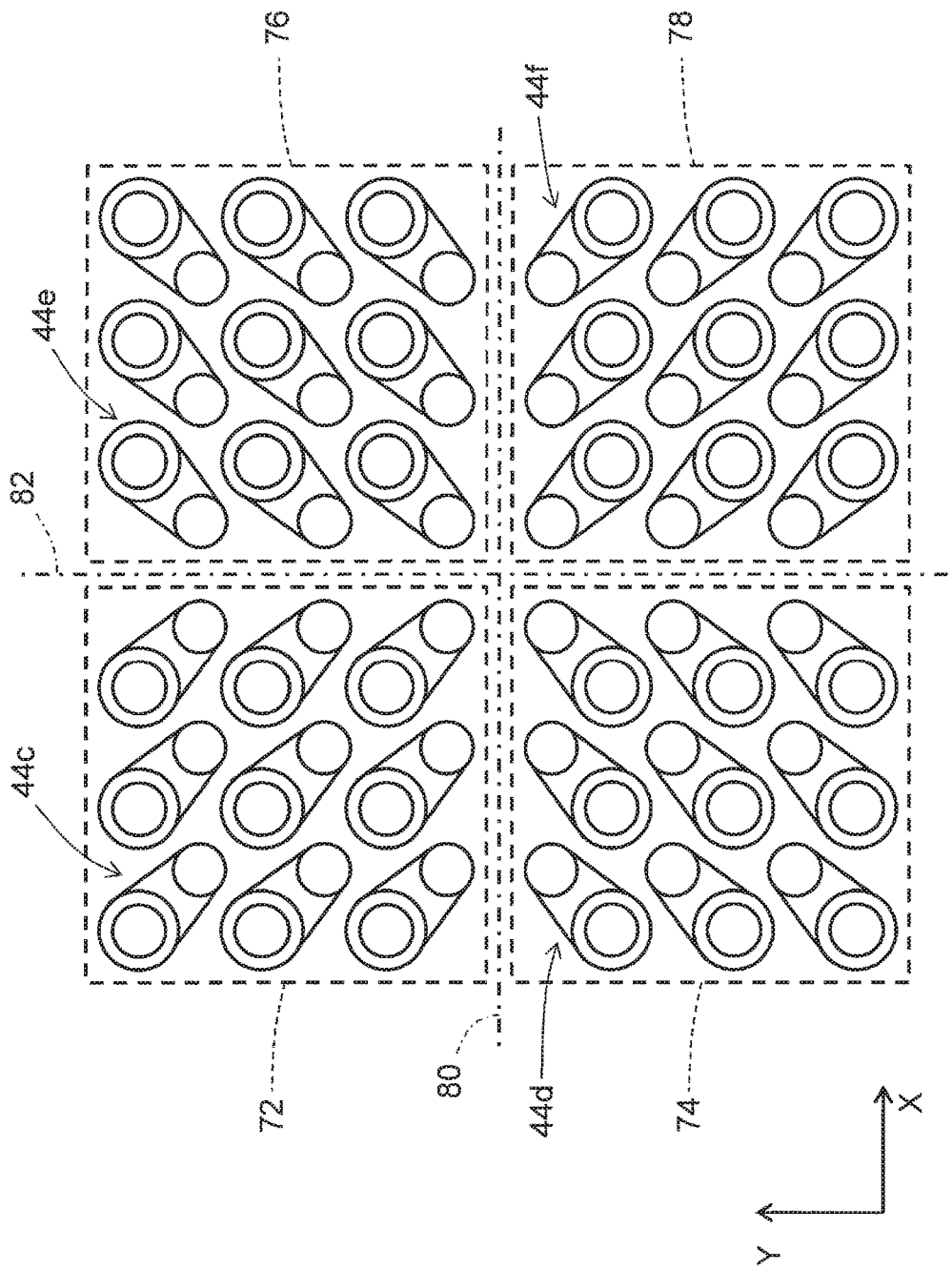
FIG. 12 is a plan view showing a layout of an electrode array according to a sixth embodiment.

An ultrasound probe according to a sixth embodiment of the present disclosure is described below. FIG. 12 shows a layout of an electrode array disposed on the ultrasound probe according to the sixth embodiment. FIG. 12 shows an XY plane, viewing the electrode array from above (from the upper surface 30a side of the relay board 30). The structure of the ultrasound probe is identical to the ultrasound probe 10 according to the first embodiment except for the electrode array.

In the sixth embodiment, the electrode array is divided into four sub-arrays (electrode sub-arrays 72, 74, 76, and 78). The electrode sub-array 72 includes two or more electrodes 44c, the electrode sub-array 74 includes two or more electrodes 44d, the electrode sub-array 76 includes two or more electrodes 44e, and the electrode sub-array 78 includes two more electrodes 44f.

For example, between a pair of the electrode sub-arrays 72 and 76 and a pair of the electrode sub-arrays 74 and 76 with a boundary 80 parallel to the X axis therebetween, the electrodes 44c, 44d, 44e, and 44f are arranged such that the board terminals 32 are disposed on the inner side (on the center side) and the vias 34 are disposed on the outer side. Between a pair of the electrode sub-arrays 72 and 74 and a pair of the electrode sub-arrays 76 and 78 with a boundary 82 parallel to the Y axis therebetween, the electrodes 44c, 44d, 44e, and 44f are arranged such that the board terminals 32 are disposed on the inner side (on the center side) and the vias 34 are disposed on the outer side.

In the CW mode, for example, the electrodes 44c and 44d respectively included in the electrode sub-arrays 72 and 74 are used as electrodes for transmission, whereas the electrodes 44e and 44f respectively included in the electrode sub-arrays 76 and 78 are used as electrodes for reception. The electrodes may be used vice versa. As another example, the electrodes 44c and 44e respectively included in the electrode sub-arrays 72 and 76 may be used as electrodes for transmission, whereas the electrodes 44d and 44f respectively included in the electrode sub-arrays 74 and 78 may be used as electrodes for reception. The electrodes may be used vice versa.

Also in the sixth embodiment, the electric crosstalk can be prevented or reduced, because of the different layouts (shift patterns) between the transmitter group and the receiver group.

By combining the sixth embodiment with the second embodiment, two of more ground electrodes 60 may be disposed along the boundaries 80 and 82. Also by combining the sixth embodiment with the third and fourth embodiments, the acoustic separation groove 64 and the acoustic separation material 66 may be formed along the boundaries 80 and 82. Further by combining the sixth embodiment with the fifth embodiment, the electrode array may be arranged such that the electrode array is divided into four sub-arrays with the transmitter lead sub-arrays and the receiver lead sub-arrays away from each other in the horizontal direction.

REFERENCE NUMERALS 10 ultrasound probe, 12 transducers, 20 backing, 22 backing body, 24 leads, 28 electronic circuit, 30 relay board, 32 board terminals, 34 vias, 44 electrodes, 46 conductive channels, 48 transmitter electrode array, 50 receiver electrode array, 52 transmitter electrode column, and 54 receiver electrode column.

The invention claimed is:

1. An ultrasound probe comprising:
   a transducer array;
   a backing comprising
      a backing body which absorbs ultrasound waves emitted from the transducer array;
      a lead array disposed inside the backing the lead array electrically connected to the transducer array, and
      a backing terminal array disposed on a surface of the backing body, the backing terminal array electrically connected to the lead array;
   an electronic circuit which processes at least, one of transmission signals supplied to the transducer array and reception signals output from the transducer array; and
   a relay board disposed between the backing and the electronic the relay board comprising an electrode array including two or more electrodes,
   wherein the electrode array comprises
      a first electrode array disposed on one side of a boundary, and
      a second electrode at-ray disposed on the other side of the boundary, the first electrode array comprises
      a first board terminal sub-array in contact with a first backing terminal sub-array in the backing terminal array,
      a first via sub-array for substrate internal wiring, the first via sub-array having a two-dimensional arrangement corresponding to a two-dimensional arrangement of the first board terminal sub-array shifted in parallel in a first direction, and
      a first conductive channel sub-array connecting the board terminal sub-array and the first via sub-array,
   the second electrode array comprises
      a second board terminal sub-array in contact with a second backing terminal sub-array in the backing terminal array,
      a second via sub-array for substrate internal wiring, the second via sub-array having a two-dimensional arrangement corresponding to a two-dimensional arrangement of the second board terminal sub-array shifted in in a second direction, and
      a second conductive channel sub-array connecting the second board terminal sub-array and the second via sub-array,
      wherein the first direction is a direction away from the boundary on one side and is oblique to a direction orthogonal to the boundary, and the second direction is a direction away from the boundary the other side and is oblique to the direction orthogonal to the boundary.

2. The ultrasound probe according to claim 1, wherein a ground terminal column is disposed at the boundary.

3. The ultrasound probe according to claim 1, wherein an acoustic separation groove is formed at the boundary.

4. The ultrasound probe according to claim 3, wherein the acoustic separation groove is filled with an acoustic separation material.

5. An ultrasound probe comprising:
a transducer array;
a backing comprising
   a backing body which absorbs ultrasound waves emitted from the transducer array;
   a lead array disposed inside the backing the lead array electrically connected to the transducer array, and
   a backing terminal array disposed on a surface of the backing body, the backing terminal array electrically connected to the lead array;
an electronic circuit which processes at least, one of transmission signals supplied to the transducer array and reception signals output from the transducer array; and
a relay board disposed between the backing and the electronic the relay board comprising an electrode array including two or more electrodes,
wherein the electrode array comprises
   a first electrode array disposed on one side of a boundary, and
   a second electrode at-ray disposed on the other side of the boundary, the first electrode array comprises
   a first board terminal sub-array in contact with a first backing terminal sub-array in the backing terminal array,
   a first via sub-array for substrate internal wiring, the first via sub-array having a two-dimensional arrangement corresponding to a two-dimensional arrangement of the first board terminal sub-array shifted in parallel in a first direction, and
   a first conductive channel sub-array connecting the board terminal sub-array and the first via sub-array,
the second electrode array comprises
   a second board terminal sub-array in contact with a second backing terminal sub-array in the backing terminal array,
   a second via sub-array for substrate internal wiring, the second via sub-array having a two-dimensional arrangement corresponding to a two-dimensional arrangement of the second board terminal sub-array shifted in in a second direction, and
   a second conductive channel sub-array connecting the second board terminal sub-array and the second via sub-array,
   wherein the first direction is a direction away from the boundary on one side and the second direction is a direction away from the boundary the other side,
wherein the lead array comprises
   a first lead sub-array electrically connected to the first backing terminal sub-array, and
   a second lead sub-array electrically connected to the second backing terminal sub-array, and
wherein the first lead sub-array and the second lead sub-array are arranged away from each other.

* * * * *